(12) United States Patent
Atkinson et al.

(10) Patent No.: US 7,842,300 B2
(45) Date of Patent: Nov. 30, 2010

(54) BONE REPAIR PUTTY

(75) Inventors: Brent L. Atkinson, Lakewood, CO (US); Tracey S. Hanks, Denver, CO (US)

(73) Assignee: DENTSPLY International, Inc., York, PA (US)

( * ) Notice: Subject to any disclaimer, the term of this patent is extended or adjusted under 35 U.S.C. 154(b) by 1056 days.

(21) Appl. No.: 10/628,692

(22) Filed: Jul. 28, 2003

(65) Prior Publication Data

US 2004/0062816 A1  Apr. 1, 2004

Related U.S. Application Data

(60) Provisional application No. 60/399,851, filed on Jul. 31, 2002.

(51) Int. Cl.
*A61L 24/00* (2006.01)
*A61L 27/46* (2006.01)
*A61L 27/56* (2006.01)
*A61L 27/58* (2006.01)

(52) U.S. Cl. .......................... 424/400; 424/426; 424/489

(58) Field of Classification Search ................ 424/400, 424/422, 489
See application file for complete search history.

(56) References Cited

U.S. PATENT DOCUMENTS

| | | | | |
|---|---|---|---|---|
| 4,770,860 | A * | 9/1988 | Ewers et al. | 423/173 |
| 4,861,733 | A | 8/1989 | White | |
| 4,938,938 | A | 7/1990 | Ewers et al. | |
| 5,290,558 | A | 3/1994 | O'Leary et al. | |
| 5,352,715 | A | 10/1994 | Wallace et al. | |
| 5,635,482 | A * | 6/1997 | Bhatnagar | 514/14 |
| 5,676,976 | A | 10/1997 | Lee et al. | |
| 5,840,290 | A | 11/1998 | Hench et al. | |
| 5,922,025 | A | 7/1999 | Hubbard | |
| 5,942,499 | A | 8/1999 | Radomsky | |
| 6,027,742 | A | 2/2000 | Lee et al. | |
| 6,030,635 | A * | 2/2000 | Gertzman et al. | 424/423 |
| 6,051,247 | A | 4/2000 | Hench et al. | |
| 6,123,957 | A | 9/2000 | Jernberg | |
| 6,190,684 | B1 | 2/2001 | Hench et al. | |
| 6,214,368 | B1 | 4/2001 | Lee et al. | |
| 6,221,854 | B1 | 4/2001 | Radomsky | |
| 6,287,341 | B1 | 9/2001 | Lee et al. | |
| 6,428,803 | B1 * | 8/2002 | Ewers et al. | 424/426 |
| 6,432,436 | B1 | 8/2002 | Gertzman et al. | |
| 6,432,437 | B1 | 8/2002 | Hubbard | |
| 6,437,018 | B1 | 8/2002 | Gertzmann et al. | |
| 6,458,375 | B1 | 10/2002 | Gertzmann et al. | |
| 6,521,264 | B1 | 2/2003 | Lacout et al. | |
| 6,533,820 | B2 | 3/2003 | Dorigatti et al. | |
| 6,548,080 | B1 | 4/2003 | Gertzmann et al. | |
| 2001/0014664 | A1 | 8/2001 | Radomsky | |
| 2001/0053938 | A1 | 12/2001 | Dorigatti et al. | |
| 2002/0071827 | A1 * | 6/2002 | Petersen et al. | 424/93.1 |
| 2002/0136696 | A1 | 9/2002 | Lee et al. | |
| 2002/0151466 | A1 | 10/2002 | Hubbard et al. | |
| 2003/0049329 | A1 | 3/2003 | Lee et al. | |
| 2003/0143283 | A1 * | 7/2003 | Tofe | 424/549 |
| 2003/0152606 | A1 | 8/2003 | Gerber | |

FOREIGN PATENT DOCUMENTS

| | | |
|---|---|---|
| DE | 10060036 | 8/2002 |
| EP | 1 080 737 | 3/2001 |
| EP | 631 499 | 5/2001 |
| EP | 1 127 581 | 8/2001 |
| EP | 1263365 | 4/2002 |
| EP | 1283693 | 8/2002 |
| EP | 637254 | 10/2002 |
| EP | 1 080 698 | 9/2003 |
| EP | 1 080 699 | 9/2003 |
| WO | 91/17777 | 11/1991 |
| WO | 99/02107 | 1/1999 |
| WO | 99/03487 | 1/1999 |
| WO | 01/12247 | 2/2001 |
| WO | 02/19937 | 3/2002 |
| WO | 02/28332 | 4/2002 |
| WO | 03/063686 | 8/2003 |

\* cited by examiner

*Primary Examiner*—Christina Bradley
(74) *Attorney, Agent, or Firm*—Douglas J. Hura; David A. Zdurne; Leana Levin

(57) ABSTRACT

A bone repair material is described that is of putty-like consistency, particularly useful for repairing dental bony defects such as those caused by bone loss resulting from moderate or severe periodontitis, augmenting of bony defects of the alveolar ridge, filling tooth extraction sites, or sinus elevation grafting. The repair material includes a porous, resorbable particulate that is bone-derived or derived from bone-like hydroxyapatite or synthetic hydroxyapatite; and, a resorbable carrier, such as high molecular weight polysaccharides, such as hyaluronic acid. A high concentration of particulate in the putty enhances bone repair and requires a high concentration of carrier to retain the putty at the defect site. For a particulate density of about 1.2 g/cc such as PEPGEN P-15® Bone Graft, a preferred formulation comprises about 55% percent by weight of the putty suspended in a hyaluronic acid gel of about $1.4 \times 10^6$ daltons molecular weight and a final concentration of about 56 mg/cc which material adheres to a bony periodontal defect and does not excessively expand or migrate from the defect when held in place by a conventional flap closure.

13 Claims, No Drawings

BONE REPAIR PUTTY

This application claims priority under 35 U.S.C. 119(e) to provisional Application No. 60/399,851, filed Jul. 31, 2002.

FIELD OF INVENTION

The present invention relates to improvements in bone repair materials employed to promote growth of bone to repair defects therein. More particularly, the bone material of the invention focuses upon enhancing treatment of dental bone defects such as bone loss from moderate or severe periodontitis, augmenting of bony defects of the alveolar ridge, filling tooth extraction sites, or sinus elevation grafting.

BACKGROUND OF THE INVENTION

In the repair of a dental bone defect such as periodontal bone loss, a treatment may include application of a composition or formulation to the defect site to enhance repair and bone healing. The composition typically includes: (1) a particulate material to provide structural support and filling of the defect; (2) compounds or medicaments to enhance repair of bone; and (3) a carrier system to facilitate delivery to and retention of the composition at the defect site for the duration of the treatment.

Selection of the particulate material depends upon its intended function in the treatment, its biocompatibility with the human body and its availability. A key limitation is whether the function of the treatment requires that the material be resorbed by natural bodily actions or remain in place as permanent supporting structures. Many formulations such as those described by Hubbard in U.S. Pat. No. 5,922,025 and related patents intend to deliver, by injection, a tissue augmentation material that is non-resorbable, for example comprising a ceramic particulate of 15-150 μm, suspended in a resorbable polysaccharide gel carrier, such as hyaluronic acid. The non-resorbable ceramic particulate is intended to effect a one-time, permanent repair that does not require repetitious treatments. Other such materials include bioactive/biocompatible glass particulates, such as described by Walker et al in WO 91/17777, also comprising an injectable gel formed of a hyaluronic acid, of at least $10^6$ daltons molecular weight. See also Hench et al in U.S. Pat. No. 5,840,290 and related patents, wherein a glass particulate is said to bond to bone at the defect site, enhancing osseous ingrowth or infiltration for repair.

Where it is desired to generate new bone to repair a defect and where immediate and continued structural support is not a limiting factor, regeneration of bone by natural body mechanisms is most desirable. The natural repair and regeneration process has long been thought to be enhanced by filling the defect with various bone derived or bone-related synthetic particulates. Gerber in German Patent Application DE 100 60 036 describes a "remodeling" mechanism wherein bone is resorbed and replaced by osteoclasts by processes termed "osteogenesis", "osteoconduction" and "osteoinduction". Gerber describes osteoconduction as bone growth arising from bone tissue that is present along a leading structure thereof; osteoinduction as a stimulation of differentiation of non-bone cells to form osteoblasts; and osteogenesis as a new formation of bone from vital, transplanted bone cells.

Gerber notes that resorbability is an essential requirement for a material that is to participate in remodeling and be replaced by natural bone within a certain time without an inflammation reaction that inhibits formation of tissue.

Of the useful bone particulates, autologous derived material, while effective and safe, is of impractical availability generally. Allogenic material is readily available and, alternatively, xenogeneic bone sources are utilized as well. Synthetic materials, principally hydroxyapatite are also available.

The various particulate bone derived materials may include naturally occurring organic components that function to induce and mediate replacement bone growth. However, there are concerns for biocompatibility and safety in allowing organic components to remain in the bone particulate material. Hence, the bone particulate may be treated by a sintering process to reduce such risks. Alternatively, the bone particulate source material may be replaced by a completely synthetic hydroxyapatite material that includes no organic residue. The difficulty arising for synthetics is that the resulting material may not resorb or otherwise lacks activity in the remodeling process.

Some researchers have focused upon providing bone or substitute particulates that have porous structures that enhance bone growth or integration. Thus, Ewers et al in U.S. Pat. No. 4,770,860 describe a resorbable porous hydroxyapatite material, derived from a lime-containing algae by means of a hydrothermal process in the presence of phosphates. In Ewers et al U.S. Pat. No. 6,428,803, the hydroxyapatite material is provided in the form of a gel obtained by a unique sol-gel process.

In the previously mentioned German Patent Application DE 100 60 036, Gerber describes a resorbable bone replacement material based upon calcium phosphates wherein the material is characterized by a "loose" crystal structure. The structure further includes various sized interconnecting pores that encourage ingrowth of collagen fibers to initiate the remodeling process.

Formulations thought to enhance repair of bone tissue may include bone growth agents. Bhatnagar in U.S. Pat. No. 5,635,482 describes a synthetic collagen-like agent that mimics autogenous cell attachment factors that promote bone growth. Bhatnagar identified and synthesized a fifteen amino acid sequence of Type I collagen that promotes migration of reparative cells from surrounding tissues; directs cell attachment and oriented migration; and facilitates a biomimetic environment for bone generation. These and related polypeptide materials, called P-15, are bound to a particulate hydroxyapatite which may be a natural, microporous xenogeneic bone mineral, such as OsteoGraf® N-300 manufactured by Dentsply Friadent CeraMed of Lakewood, Colo. In order for the P-15 cell binding poly peptide to be active, it must be bound irreversibly to the particulate. Bhatnagar teaches that the resulting dry particulate matrix including P-15, trade marked PEPGEN P-15® Bone Graft and sold by Friadent CeraMed may be combined with a carrier such as PBS or a hydrogel for placement, for example, in an intrabony defect in a tooth supporting structure.

The literature includes a number of formulations including other "growth factors" that function differently from P-15, in that the factors are not bound to the particulate but in solution. Radomsky in U.S. Pat. No. 5,942,499 and related patents claim increasing bone growth rate or magnitude directly, without the presence of active bone particulates or the like, by combining bFGF with hyaluronic acid. Radomsky distinguishes his formulation from the known effectiveness of demineralized bone matrix (DBM) alone or DBM in combination with hyaluronic acid. Radomsky claims enhancing bone repair, depending solely upon the combination of bFGF with hyaluronic acid to promote growth amount. Gertzmann et al in U.S. Pat. No. 6,030,635 utilizes an allogenic bone particulate that is demineralized comprising essentially collagen, further containing active "bone morphogenic proteins" (BMP), wherein the resulting formulation is said to be osteoconductive and osteoinductive, with the DBM particulate being remodeled into natural bone. The formulation includes less than about 50% by weight DBM suspended in hyaluronic acid, having a molecular weight of $7 \times 10^5$-$3 \times 10^6$ daltons, to form a hydrogel that is a malleable putty. Higher concentrations of DBM in the Gertzmann formulation result in poor formability, too grainy and too dry for convenient placement.

In general, formulators of bone treatment materials have directed a great deal of effort to improve handling characteristics through selection of an appropriate carrier for delivering the bone repair material to the defect site. It is desirable that the bone repair material be easily placed, but not be allowed to migrate from the defect. In addition, and primarily, bone formation must not be inhibited by the carrier. That is, the carrier materials for the bone repair material must be biocompatible and not interfere with the mediated bone formation, while helping provide adequate spacing between the repair material particulates to allow for cell and vascular infiltration. The carrier material should biodegrade and be resorbed. However, too fast a degradation rate is not preferred since cellular and vascular infiltration cannot develop. Too slow of a resorption rate also interferes with cellular migration, vascular penetration and bone formation.

As described by Bhatnagar, as well as the others cited above, preferred carriers are hydrogels that incorporate the bone particulate and any growth enhancing agent. Preferred hydrogels include polysaccharides, particularly those of high molecular weight, preferably greater than $10^6$ daltons. A most particularly preferred carrier is hyaluronic acid and its derivatives. While much of the prior systems have required injectability as a key handling characteristic, compositions that have a putty consistency are particularly useful in treating periodontal and related bone loss defects.

In a typical periodontal surgical bone repair procedure or method, an incision is made in the gum tissue to expose a bone defect adjacent to a tooth root. Once the defect and root are debrided, a bone repair material, such as the aforementioned PEPGEN P-15 bone graft material, suspended in a suitable carrier is placed. The gum tissue is then closed, maintaining the repair material in place. See Bowen et al in "Comparison of Decalcified Freeze-Dried Bone Allograft and Porous Particulate Hydroxyapatite in Human Periodontal Osseous Defects", J. Periodontology (May 1989). Optionally, a barrier material may be utilized to retain the repair formulation in contact with the defect.

There remains a need for bone repair treatment formulations that comprise a putty consistency with high concentrations of resorbable bone or bone-like particulate in a high concentration carrier that when applied to the defect site remains adhered thereto without migration or excessive expansion.

SUMMARY OF THE INVENTION

It is an object of the invention to provide a bone repair material or composition that includes: a porous, resorbable particulate, derived from bone or bone-like hydroxyapatite or synthetic hydroxyapatite; and a resorbable carrier gel component, for placing in a bony defect wherein bone repair is facilitated, said bone repair material of a putty-like consistency. Preferably the bone repair material composition or formulation comprises a high concentration of particulate material, comprising 30-75 weight percent of the putty depending upon the particulate density, requiring a high concentration of carrier component to maintain said particulate in the putty.

Further, the invention provides a bone repair formulation that does not significantly expand in contact with biological fluids, does not migrate from the site of application and does not interfere with bone formation.

It is an object of the invention to provide a bone repair formulation that is moldable and adhesive at room temperature, maintains the bone repair particulate in suspension for sufficient time to enhance bone growth, is not immediately solubilized or swelled by biological fluids and does not dry out too rapidly. The bone repair formulation of the invention is preferably in the form of a putty that may be trowelled into place using a spatula, placed by syringe or even hand molded into the bony defect to be repaired. The putty maintains the bone repair particulate in a suspension matrix and does not migrate from the defect placement.

A preferred bone repair or implant material of the invention particularly useful for repairing periodontal defects, in addition to including a bone-like hydroxyapatite mineral particulate, preferably includes a P-15 polypeptide synthetic biomimic of Type I collagen bone growth enhancer, having at least one of the peptide sequences described in Bhatnagar, U.S. Pat. No. 5,635,482, bound to said particulate.

The formulation of the invention includes a carrier component for suspending said particulate mixture, forming a moldable, putty-like formulation for placing in a periodontal bone defect, wherein bone growth repair is facilitated. A preferred carrier component is a polysaccharide such as hydroxylpropyl cellulose or methyl cellulose or the like. Particularly preferred are mucopolysaccharides, such as hyaluronic acid and its derivatives. The carrier selected is of high molecular weight and in a sufficiently high concentration in the putty to suspend the high concentration of particulate in the putty, said concentration preferably 45-64 mg/cc.

In a most preferred formulation, the collagen poly peptide treated particulate comprises about 55% by weight of the formulation and 45% by weight of a hyaluronic acid gel carrier of sufficient molecular weight, preferably $0.7$-$2 \times 10^6$ daltons, that the formulation forms a viscous, moldable putty. A key advantage of the carrier is that the particulate, once placed, remains uniformly suspended, does not settle or separate substantially from the carrier, does not significantly swell after placement in a bone defect repair and where particles do not migrate away from putty.

DESCRIPTION OF THE PREFERRED EMBODIMENTS

The invention is a composition or formulation of a bone repair material and a method of using the material to repair defects in bones. It is particularly suited for use in enhancing regeneration of bone and repairing dental bony defects such as in treating periodontal disease where alveolar bone is eroded and support for adjacent teeth has been destroyed or is seriously threatened. It is further useful in augmenting bony defects of the alveolar ridge, filling tooth extraction sites, and sinus elevation grafting.

The invention provides a bone repair or graft formulation that includes a porous, resorbable particulate, derived from bone or synthetic or natural bone-like material, that forms a matrix structure to enhance and temporarily support new bone growth. The particulate material may be derived from an allograft, xenogeneic or other natural bone-derived material, for example. A preferred xenogeneic material is any of the porous, resorbable bone graft materials, such as sold under the PEPGEN P-15® or OsteoGraf® marks and manufactured by Dentsply Friadent CeraMed. OsteoGraf® is an organic, natural, microporous, bovine-derived bone mineral, while PEPGEN P-15® includes a P-15 poly peptide sequence described by Bhatnagar in U.S. Pat. No. 5,635,482, irreversibly bound to a natural microporous, xenogenic bone material OsteoGraf®/N 300. The PEPGEN P-15® bone graft material typically has a particle size of 250-420 microns. Over time, the particulate material is resorbed and remodeled into natural bone, remaining only temporarily to provide a structure that is completely integrated by new bone tissue.

In another embodiment, the porous resorbable bone-like material is ALGIPORE® or ALGISORB® hydroxyapatite, also sold by Dentsply Friadent CeraMed, derived from lime-containing algae in accord with Ewers, et al U.S. Pat. Nos. 4,770,860 and 6,428,803, the disclosures of which are incorporated by reference in their entirety.

The invention preferably provides a bone growth enhancing composition, most preferably comprising the P-15 polypeptide sequences described by Bhatnagar in U.S. Pat. No. 5,635,482 and its continuations and divisions, wherein P-15 is a synthetic biomimetic of a fifteen amino acid sequence of Type I collagen that is uniquely involved in the binding of cells, particularly fibroblasts and osteoblasts. The P-15 material promotes the migration of reparative cells from surrounding tissues; directs cell attachment and oriented migration; and facilitates a biomimetic environment for bone generation. Any of the synthetic polypeptide sequences described or claimed in U.S. Pat. No. 5,635,482 and its various continuations/divisions thereof are suitable, and their disclosures are incorporated herein by reference.

An effective formulation includes a high concentration of particulate for maintaining the formulation at the defect site. A high concentration of particulate results in higher bone formation. More particulate retained at a site increases the concentration of bone growth enhancing agent, such as P-15 at the defect site, since P-15 is bound to the particulate. The concentration of PEPGEN P-15 may range 800-960 mg/cc, including about 880 mg/cc for the preferred 55% by weight composition where PEPGEN P-15 is the putty particulate.

There is a direct relationship between the weight percentage of particulate present in the applied putty formulation and the bulk density of the particulate. A successful putty formulation, for example, includes 55% by weight of the preferred PEPGEN P-15 composition having a particulate component of OsteoGraf®/N 300 having a bulk density of 1.2 g/cc. A successful putty formulation, including ALGIPORE particulate, having a bulk density of 0.5 g/cc, comprises 35-40 weight percent ALGIPORE particulate.

A key element of the invention is that a carrier is provided, in combination with a desired amount of bone particulate, wherein a putty is formed that is moldable, easy to handle and place in a dental bony defect. Especially, the putty upon placement remains substantially fixed and adhered in place without migrating into adjacent tissues. The carrier is resorbed after a period of time but maintains its structural integrity long enough to help provide structure for placement of the graft and for bone to form. The carrier material must be biocompatible, even at relatively high concentrations that are necessary to achieve a formulation that does not excessively change dimensions. Dimensional stability of the formulation; i.e., neither significantly expanding nor shrinking, is also a key feature of the invention.

Preferred carrier compositions are polysaccharides, including mucopolysaccharides. Of the polysaccharides, hydroxylpropyl cellulose (HPC) and methyl cellulose are suitable. Of the mucopolysaccharides, hyaluronic acid and its derivatives are preferred. Useful carriers are typically of high molecular weight. The preferred hyaluronic acids and derivatives typically are $0.7\text{-}2.0\times10^6$ daltons, preferably $1.0\text{-}1.8\times10^6$ daltons.

The carrier component selected must be present in a relatively high concentration to contain the desired high concentration of particulate and yet maintain desired putty characteristics and retain the particulate at the defect site. Concentrations of the preferred hyaluronic acid are on the order of 45-64 mg/cc in the putty. Such higher carrier concentration forms a preferred putty even at 55 weight percent or greater for the PEPGEN P-15 particulate, in contrast to prior art formulations which are too dry or grainy when approaching 50% particulate of comparable density.

The dental bone augmentation and bone repair putty of the invention may be utilized in treating sinus elevation defects, extraction sites, bone loss around implants and to support implant placement, extraction site ridge preservation, repair periodontal intrabony defects, pre-existing defects around implants, ridge augmentation, ridge onlay, repair furcation defects, to cover exposed implant surfaces or threads, or to repair an edentulous site to facilitate implant acceptance.

For example, a sinus elevation defect is a lack of available bone height in the maxillary posterior, due to bone resorption after tooth loss. Grafting the floor of the sinus increases available bone height allowing for ideal implant placement. An incision is made from the posterior tuberosity slightly palatal to the crest of the ridge to the canine area exposing the lateral antral wall. A lateral window is created through the cortical bone and then the Schneiderian membrane is gently lifted and positioned superiorly, creating access for recipient graft. PEPGEN P-15 graft putty material of the invention is packed into the subantral space anteriorly, medially and posteriorly. The high particle concentration within the putty of the invention assists in lifting the Schneiderian membrane. The flap is repositioned and sutured. Membrane use is at the discretion of the clinician.

In treating extraction socket defects, a tooth is atraumatically extracted, preserving the bony socket walls as much as possible. Thorough debridment, curettage, irrigation and aspiration of the socket is essential and all bleeding should be under control. PEPGEN P-15 graft putty of the invention is then placed into the lower portion of the socket and gently packed to insure intimate contact between the graft material and the bony walls. The remainder of the socket is then filled to the height of the alveolar crest. PEPGEN P-15 putty of the invention provides spacing to insure vascularization through the graft. Primary closure is preferable but not essential to the success of the graft. A containment device or membrane may be placed over the graft to contain the material in the socket. A simple suture (4 to 6 point closure) assists in healing.

Deficient alveolar ridges require augmentation to provide adequate bone for implant placement. An incision is created over the deficient area and the ridge exposed. After elimination of all periosteum and soft tissue, the cortical bone should be prepared to receive the graft material. Preparation includes cortical fenestration to allow bleeding and the release of bone marrow. PEPGEN P-15 graft putty of the invention is gently packed onto the ridge and approximated over the deficient bony structure. The flap is repositioned over the graft and the primary closure of the tissue completed. Membrane use is at the discretion of the clinician.

Endosseous implants must be stable in the bony ridge and exposure of the implant through the bone is detrimental to the success of the implant. If a portion of the implant is exposed by a dehiscence defect, for example, through the bone, bone replacement graft material can be used to repair the site and regenerate new bone to cover the implant. Incisions are made through the soft tissue to expose the dehiscence. Depending upon the surface coating of the implant, detoxification of the implant may be necessary to thoroughly clean and prepare the implant to receive the graft. PEPGEN P-15 graft putty of the invention is packed over the exposure of the implant to assist in bone regeneration and stability of the substrate. The flap is repositioned and primary closure is essential to the success of the graft.

The examples below further describe embodiments of the compositions of the invention and methods of their use. The examples are not intended to limit the scope of the invention but are illustrative only.

EXAMPLE 1

Hyaluronic Acid Gel 60 grams of PEPGEN P-15® bone graft material supplied by Dentsply Friadent CeraMed of Lakewood, Colo., comprising a P-15 poly peptide sequence described by Bhatnagar in U.S. Pat. No. 5,635,482, irreversibly bound to a natural microporous, xenogenic bone material OsteoGraf®/N 300, was weighed out into a container. 40 grams of hyaluronic acid gel, having a molecular weight of $7\times10^5$ daltons, supplied by Hyaluron Corporation of Woburn, Mass., was mixed with the PEPGEN P-15 material by means of a spatula to homogeneity. The resulting material is of a moldable, putty-like consistency, wherein the particulate remains suspended in the putty gel even when spun in a centrifuge (3,000 rpm for 30 minutes) The resulting putty of the 60:40 material had a density of 1.664 +/−0.0533 g/cc. The concentration of hyaluronic acid component in the putty is about 47 mg/cc, and the concentration of active PEPGEN P-15 is about 960 mg/cc.

EXAMPLE 2

Hydroxylpropyl Cellulose Gel 7 grams of hydroxylpropyl cellulose, hereinafter abbreviated HPC, having a molecular weight of about 1,150,000 daltons, supplied by Hercules (Klucel, HF Pharma), was added to 93 grams of water or isotonic saline and immediately mixed by hand. The mass was re-mixed after 2-3 minutes and re-mixing was repeated until a gel was formed, which was held overnight at 4-8° C. 55 grams of PEPGEN P-15 was added to 45 grams of the HPC gel and mixed with a spatula until uniform. The resulting formulation was:

| | |
|---|---|
| PEPGEN P-15 particles | 55.00 grams |
| HPC | 3.15 grams |
| Water or Isotonic Saline | 41.80 grams |

The resulting putty mass had a density in saline of 1.647+/−0.0452 g/cc.

EXAMPLE 3

Methyl Cellulose Gel

The process of Example 2 was repeated except that methyl cellulose manufactured by Dow Chemical (Methocel A, A4CP) was substituted. The resulting formulation was:

| | |
|---|---|
| PEPGEN P-15 particles | 55.00 grams |
| Methyl Cellulose | 3.60 grams |
| Glycerol | 6.75 grams |
| Water | 34.60 grams |

The resulting formulation was autoclavable with no noticeable changes in handling of original characteristics. The material did not substantially expand in PBS or water.

EXAMPLE 4

Hyaluronic Acid Gel

The method and formulation of Example 1 was repeated except that PEPGEN P-15 graft comprised 55% by weight and a hyaluronic gel of greater MW comprised 45% by weight of the formulation. To make the gel, 92% sodium phosphate buffer was blended together with 8% hyaluronate by weight to homogeneity. To make 1 cc of putty, 0.55 grams of PEPGEN P-15 was thoroughly mixed with 0.45 grams of hyaluronic acid gel. A preferred high molecular weight hyaluronic acid of $1.2$-$1.7\times10^6$ daltons was employed, resulting in a concentration of about 57 mg/ml. The concentration of PEPGEN P-15 was about 880 mg/cc in the putty.

EXAMPLE 5

Hyaluronic Acid Gel/ALGIPORE Particulate 0.40 grams of ALGIPORE bone graft particulate, supplied by Dentsply Friadent CeraMed of Lakewood, Colo., comprising the P-15 peptide sequence of Example 1 bound to the ALGIPORE particulate was mixed with 0.60 grams of a gel comprising a hyaluronic acid, prepared as described in Example 4 and having a molecular weight of $1.2$-$1.7\times10^6$ daltons. Two sizes of ALGIPORE were tested: 0.3-0.5 mm and 0.5-1 mm. The concentration of ALGIPORE P-15 in the putty was 440 mg/cc for the 0.3-0.5 cc size and 480 mg/cc for the 0.5-1.0 cc size. The concentration of hyaluronic acid component in the putty was about 53 mg/cc for the 0.3-0.5 cc size and for the 0.5-1.0 cc size. The ALGIPORE component comprised 40 percent by weight of the putty, the formulation comprising:

| | |
|---|---|
| ALGIPORE P-15 Particulate | 0.400 grams |
| Hyaluronic Acid | 0.048 grams |
| 10 mM Sodium Phosphate | 0.552 grams |

EXAMPLE 6

Carboxymethyl Cellulose Gel

A gel comprising carboxymethyl cellulose (CMC), supplied by Hercules (Aqualon 7HFPH) having a MW of about 700,000 daltons and a viscosity of 1500-2500 cp, glycerol and water of the following composition was formed to make a carrier gel of a commercial bone graft material. 37.5 grams of PEPGEN P-15 graft was added to 62.5 grams of the CMC gel and mixed until a homogenous blend resulted, yielding about 100 grams of a PEPGEN P-15® Flow™ product. The resulting formulation was:

| | |
|---|---|
| PEPGEN P-15 Particulate | 37.50 grams |
| CMC | 1.97 grams |
| Glycerol | 9.08 grams |
| Water | 51.45 grams |

EXAMPLE 7

Bench Top Evaluation of Handling

Samples of the invention were formulated as described in the examples above, having the compositions shown in the table below. These putties were evaluated by a panel of clinicians for handling characteristics. Table 1 shows the reported average scores. Example 4 having the highest molecular weight of the hyaluronic acid component of 1.2-1.7×10⁶ daltons and the highest hyaluronic acid concentration was deemed to have the most preferred handling characteristics of the samples tested.

TABLE 1

Handling Characteristics

| Putty Examples # | Particulate[1] Bone Material % by weight | Carrier Gel Material, % by weight gel | Description/Evaluation[2] | | |
|---|---|---|---|---|---|
| | | | Moldability | Cohesiveness | Stickiness |
| 1 | 60.0% | HY[3], 40.0% | 3.0 | 2.7 | 2.7 |
| 2 | 55.0% | HPC, 45.0% | 2.0 | 2.3 | 3.0 |
| 4 | 55.0% | HY, 45.0% | 3.0 | 3.0 | 3.0 |

[1]Particulate Bone Material was PEPGEN P-15 graft
[2]Evaluation Scale: 1 = poor; 2 = acceptable; and 3 = good
[3]Hyaluronic Acid

EXAMPLE 8

Dog Study to Evaluate Handling and Efficacy—Extraction Sockets

A 21.8 kg female dog approximately 1-2 years old was conditioned and approved for use by the USDA. The lower right quadrant of the jaw was anesthetized with 2% xylocaine. Sucular incisions were made on P2, 3 and 4 teeth. Each crown was sectioned with a fissure bur and the three teeth were extracted. The tissue was released on the lingual and buccal sides. Bleeding in the site was controlled with sterile gauze and the grafting material was tapped into the extraction socket to the height of the crest of the bone. The putty formulations described in Example 7 were employed to fill the extracted tooth sockets. Putty Example 1 was packed into P4 anterior and distal. Putty Example 2 was packed into P3 anterior and posterior.

After up to 30 minutes the filled socket was observed for expansion. Thereafter the filled socket defect was closed by suture.

In a second dog, identically prepared to the first, putty Example 4 was packed into P4 anterior and distal. After fifteen minutes, no significant expansion of the graft was observed. The defect was then closed by suture.

The time elapsed until any noticeable expansion adjacent the socket for the examples was observed and is reported in Table 2.

It is noted that the extraction socket model in the dog is characterized by elevated blood flow at high hydrostatic pressure which highlights the benefits of lower expansion. The low expansion benefit, which is a key feature of the invention, is also useful at other dental bone graft treatment sites. For example, in ridge onlays, the preferred putty of Example 4 does not expand while Putty from Example 1 does exhibit expansion.

The following observations were made: Putty from Example 1—The material accepted being in the bloody site and was able to be manipulated with surgical instruments and sterile, dry gauze. There was also minimal particle displacement. Putty from Example 2—This material did not hold together as well in the defect. However, it could be pieced together easily. The product was amenable to manipulation with instruments and sterile, dry gauze. The graft of Example 6 including a CMC carrier, known in the prior art, expands substantially and quickly in contrast to the hyaluronic acid and HPC carrier grafts which did not swell substantially and was much slower to show expansion. The preferred formulation of Example 4, including a high molecular weight hyaluronic acid gel carrier also exhibited insubstantial expansion.

The graft sites were examined histologically after 2 and 5 weeks. Block tissue samples were placed in vials containing 10% zinc formalin and processed including decalcification, embedding in paraffin, sectioning and staining with hematoxylin and eosin. The histological sections were evaluated subjectively for bone formation. Excellent, good, fair and poor ratings were applied for the speed and amount of bone repair in sockets and the interaction of the graft material with the healing tissues. The results are reported in Table 3.

TABLE 2

Observations of Graft Expansion

| Formulation, Carrier | Time elapsed until noticeable expansion in socket, minutes | Volume expanded after 15 minutes |
|---|---|---|
| Example 6, CMC | 2-3 | 30-40% |
| Example 1, HY (7 × 10⁵ MW) | 10 | 25% |
| Example 2, HPC (1.1 × 10⁶ MW) | 15 | 5-10% |
| Example 4, HY (1.2-1.7 × 10⁶ MW) | 15 | 5-10% |

TABLE 3

| Observations of Bone Repair | | |
|---|---|---|
| Putty Examples | 2 weeks | 5 weeks |
| #1 | Fair | Good |
| #2 | Poor | Fair |
| #4 | Fair | Good |
| DBM | Poor | N/D |

Putties of Examples 1 and 4 containing high amounts of particulate graft material in hyaluronic acid gel produced better bone than other compositions. Specifically, these preferred formulations produced faster and more bone than the "DBM" formulation of demineralized allograft bone particulate suspended in a 2% hyaluronic acid/saline gel, described by Gertzmann in U.S. Pat. No. 6,030,635.

EXAMPLE 9

Dog Study to Evaluate Handling in Ridge Onlay/Flap Model

Dogs were prepared in a manner similar to Example 8. In a first dog, the jaw site was anesthetized with 2% xylocaine. A beveled incision was made distal of C to mesial of P4. Vertical incisions were made and a full thickness flap was reflected. A tissue bur was utilized to perforate the cortical plate.

Putty #1, having the composition of Example 1 described above, was molded to a thickness of 6 mm and placed where it readily adhered as positioned. The flap was closed with 4-0 vicryl. Upon the first center suture, some excess material extruded out through the distal wound opening, which was thereafter sutured closed. After 10-15 minutes, the flap was reopened and the condition of the material observed. The material remained as placed and there was minimal migration and particle loss. Some expansion was observed.

Putty #2, having the composition of Example 2 described above, was molded to a thickness of 6 mm deep and placed where it readily adhered. The flap was closed with 4-0 vicryl. Upon the first center suture, the material did not extrude out through distal wound opening. After 10-15 minutes, the flap was reopened and observed to have remained as placed with minimal migration and particle loss. No substantial expansion was observed.

In a second dog, identically prepared as the first, the preferred putty #4, having the composition of Example 4 above, was molded to the top of exposed bone. Upon flap closure the material did not extrude from the distal openings. After 10 minutes the flap was reopened and the material was observed to have remained as placed. There was minimal particle migration or loss. No substantial expansion was observed.

EXAMPLE 10

Dog Study to Evaluate Handling in Defect Around Implant

Dogs were prepared in a manner similar to Example 8. In a first dog, the jaw area was anesthetized with 2% xylocaine. Teeth were extracted from the lower right quadrant. A buccal dehiscence or defect was created with a fissure bur and ronjour in all three distal sockets. The sockets were cleaned, irrigated and aspirated. A Calcitek hydroxyapatite coated implant cylinder (4×10 mm) was placed. Implant osteotomy sites were created in the distal sockets of each tooth site.

Putty #2, having the composition of Example 2 above, was placed into P4 posterior. The material broke apart during placement, but was easily reformed. The putty was in contact with irregularities of socket and implant. The putty maintained the newly formed buccal plate.

Putty #1, having the composition of Example 1 above, was placed into P3 posterior. The material handled well during placement and was in contact with irregularities of socket and implant. The putty maintained the newly formed buccal plate.

In a second dog identically prepared as the first, the preferred putty, having the composition of Example 4 above, was placed into both P2 and P3 posteriors. The material handled well during placement and was in contact with irregularities of socket and implant. The putty maintained the newly formed buccal plate. In addition, no particle migration or expansion was observed.

EXAMPLE 11

Bulk Density and Particulate Concentration

The following commercially available bone-derived particulate materials were placed into a preferred HPC or the preferred hyaluronic acid gel carrier: Bio-Oss, OsteoGraf/LD, PEPGEN P-15, (OsteoGraf/N-300), OsteoGraf/D and ALGIPORE. Each of the particulate materials was added to the gel carrier until the desired putty consistency was achieved. The particle bulk density and putty particulate concentration required to reach the desired putty consistency is shown below:

| Bone Graft Particulate | % (w/w) Particulate of Putty Formulation | Bulk Particulate Density (g/cc) |
|---|---|---|
| Bio-Oss* | 30 | 0.5 |
| OsteoGraf/LD** | 40 | 0.8 |
| PEPGEN P-15** | 55 | 1.2 |
| (OsteoGraf/N-300**) | | |
| OsteoGraf/D** | 75 | 2.2 |
| Algipore** (0.3-0.5 mm) | 35-40 | 0.5 |
| Algipore** (0.5-1.0 mm) | 35-40 | 0.6 |

*not a trademark of Dentsply Friadent CeraMed
**trademarks of Dentsply Friadent CeraMed The table shows that there is a positive relationship between optimal particulate percentage to make a putty formulation and the particulate bulk density.

The Bio-Oss material manufactured by OsteoHealth is an anorganic bovine mineral of 0.25-1.00 mm derived from cancellous bone that is more porous and less dense than PEPGEN P-15 graft particulate. A 30% (w/w) composition of Bio-Oss with HPC gel or the preferred hyaluronic acid composition formed a consistency similar to the preferred putty of 55% PEPGEN P-15. A 45% Bio-Oss containing putty was too crumbly and not preferred. A 25% Bio-Oss containing putty was too thin to be moldable.

For PEPGEN P-15 graft particulate putties formed with the HPC or hyaluronic acid carrier gel, 40%-45% PEPGEN P-15 containing formulation had a density of 1.4 g/cc and was not of a putty consistency. At 50%, the consistency was more like a putty. A preferred formulation and putty consistency comprises 55% by weight and had a density of 1.5-1.6. A preferred putty including ALGIPORE had a density of 1.1 g/cc for the 0.3-0.5 or the 0.5-1.0 mm size particles.

Various modifications and alternations of the above embodiments will be apparent to those skilled in the art without departing from the scope and spirit of the invention. It should be understood that this invention is not limited to the illustrative embodiments set forth above.

What is claimed is:

1. A bone repair putty material, comprising:
   a porous, resorbable particulate selected from an organic bone mineral, a natural bone-derived material, and a synthetic hydroxyapatite, said particulate in a concentration of 55 to 60 weight percent and having a bulk density of 1.1 to 1.3 g/cc; and
   a resorbable carrier gel component for suspending said particulate, forming a putty formulation, for placing in a bony defect, said gel component having a sufficiently high molecular weight and concentration in the putty such that bone repair is facilitated while migration and expansion of said particulate is minimized.

2. The bone repair material of claim 1 wherein said resorbable particulate is bovine-derived having a particle size range of 250 to 1000 μm.

3. The bone repair material of claim 1 wherein said resorbable particulate is a porous hydroxyapatite derived from lime-containing algae, having a particle size range of 300-1000 μm.

4. The bone repair material of claim 1, wherein said carrier gel component comprises a polysaccharide.

5. The bone repair material of claim 4, wherein said carrier gel component is hyaluronic acid or its derivatives, or hydroxylpropyl cellulose or mixtures thereof.

6. The bone repair material of claim 5, wherein said carrier gel component is hyaluronic acid or its derivatives having a molecular weight of $0.7$-$2.0 \times 10^6$ Daltons and a final concentration of 45-64 mg/cc in the putty.

7. The bone repair material of claim 1, further comprising at least one P-15 synthetic biomimetic, polypeptide sequence of Type I collagen bound to said particulate.

8. A bone repair putty material for dental bone repair procedures, comprising:
   a porous, resorbable particulate selected from a synthetic, bone-like hydroxyapatite and an organic bone-derived particulate, said particulate in a concentration of 55 to 60 weight percent and having a bulk density of 1.1 to 1.3 g/cc; and
   a hyaluronic acid gel, wherein said material is a moldable, cohesive putty for application to bony defects.

9. The bone repair material of claim 8, wherein said bone repair material comprises 55 weight percent particulate and 45 weight percent hyaluronic acid gel.

10. The bone repair material of claim 4, wherein said carrier gel is a hydroxylpropyl cellulose or methyl cellulose gel forming a moldable, cohesive putty.

11. The bone repair material of claim 8 further comprising a P-15 polypeptide sequence of collagen bound to the porous, resorbable particulate, wherein said particulate is a xenogenic bone mineral particulate of about 200-500 mm in diameter.

12. The bone repair material of claim 3 further comprising a P-15 polypeptide sequence of collagen bound to said porous hydroxyapatite derived from lime containing algae of about 300-1000 μm in diameter, and wherein said carrier is hydroxylpropyl cellulose or hyaluronic gel carrier.

13. The bone repair material of claim 7, wherein the concentration of P-15 synthetic biomimetic, polypeptide sequence of Type I collagen in the putty is at least 800 mg/cc.

* * * * *